US005644030A

United States Patent [19]
Faulmann

[11] Patent Number: 5,644,030
[45] Date of Patent: Jul. 1, 1997

[54] GENE AND METHOD FOR PRODUCTION OF AN IGA BINDING PROTEIN

[75] Inventor: Ervin Faulmann, Holland, Ohio

[73] Assignee: Medical College of Ohio, Toledo, Ohio

[21] Appl. No.: 430,024

[22] Filed: Apr. 27, 1995

Related U.S. Application Data

[62] Division of Ser. No. 108,828, Aug. 18, 1993, Pat. No. 5,413,918, which is a continuation of Ser. No. 677,209, Mar. 29, 1991, abandoned.

[51] Int. Cl.⁶ .................................................. C07K 14/315
[52] U.S. Cl. ............................................. 530/350; 530/402
[58] Field of Search .............................. 435/69.1, 69.7, 435/240.2, 252.3, 320.1; 530/350, 402; 536/23.4

[56] References Cited

U.S. PATENT DOCUMENTS 4,757,134  7/1988  Blake et al. ................................ 530/350

OTHER PUBLICATIONS

Heden et al. Eur. J. Immunol. 1991. 21, 1481–1490.
Bunn–Moreno, M.M. et al. (1981) "Lectin(s) Extracted from Seeds of *Artocarpus integrifolia* (Jackfruit): Potent and Selective Stimulator(s) of Distinct Human T and B Cell Functions" Journal of Immunology 127(2):427–429.
Kondoh, H. et al. (1986) "Jacalin, a jackfruit lectin, precipitates IgA1 but not IgA2 subclass on gel diffusion reaction" Journal of Immunological Methods 88:171–173.
Jelinkova, J. (1977) "Group B Streptococci in the Human Population" Current Topics in Microbiology and Immunology 76:127–165.
Lim, D.V. et al. (1986) "Reduction of Morbidity and Mortality Rates for Neonatal Group B Streptococcal Disease through Early Diagnosis and Chemoprophylaxis" Journal of Clinical Microbiology 23(3):489–492.
Boyer, K.M., S.P. Gotoff (1986) "Prevention of Early–Onset Neonatal Group B Streptococcal Disease with Selective Intrapartum Chemoprophylaxis" The New England Journal of Medicine 314(26):1665–1669.
Christensen, P. V.–A. Oxelius (1975) "A Reaction Between Some Streptococci and IgA Myeloma Proteins" Acta. Path. Microbiol. Scand. 83:184–188.
Russell–Jones, G.J., E.C. Gotschlich (1984) "Identification of Protein Antigens of Group B Streptococci, with Special Reference to the Ibc Antigens" J. Exp. Med. 160:1476–1484.
Russell–Jones, G.J. et al. (1984) "A Surface Receptor Specific for Human IgA on Group B Streptococci Possessing the Ibc Protein Antigen" J. Exp. Med. 160:1467–1475.
Cleat, P.H., K.N. Timmis (1987) "Cloning and Expression in *Escherichia coli* of the Ibc Protein Genes of Group B Streptococci: Binding of Human Immunoglobulin A to the Beta Antigen" Infection and Immunity 55(5):1151–1155.
Brady, L.J., M.D.P. Boyle (1989) "Identification of Non–Immunoglobulin A–Fc–Binding Forms and Low–Molecular–Weight Secreted Forms of the Group B Streptococcal β Antigen" Infection and Immunity 57(5):1573–1581.
Lindahl, G. et al. (1990) "Characterization of an IgA Receptor from Group B Streptococci: Specificity for serum IgA" Eur. J. Immunol. 20:2241–2247.
Heden, L. et al. (1991) "Molecular characterization of an IgA receptor from group B streptococci: Sequence of the gene, identification of a proline–rich region with unique structure and isolation of N–terminal fragments with IgA–binding capacity" Eur. J. Immunol. 21:1481–1490, (sequence only).

Primary Examiner—Marianne P. Allen
Assistant Examiner—Karen E. Brown
Attorney, Agent, or Firm—Saliwanchik, Lloyd & Saliwanchik

[57] ABSTRACT

The subject invention concerns novel polynucleotide sequences which code for polypeptides which bind IgA. A further aspect of the invention are hybrid proteins (and genes encoding these hybrid proteins) which comprise binding domains for both IgA and IgG.

10 Claims, 9 Drawing Sheets

```
                    A        B           C
                 |--------|------|----------------|
              Hind III  EcoR V  Bgl II           Pst I Hind III
   1 AAGCTTATGCTTGTCAATAATCACAAATTGTAGATCACTTCCTTTTTAGGACTGTAAAGCATCCTAATT
  71 ACTTTTAAATATATTACCAGAACTAGTTGGTTTGGCCCCTGTGAGTCATGCTTATGTGACATTCATCTT
 141 TATTTTTCCTGTCTATGCGGTTATCTTTTATCAAAGAATAGCAGAGGAAGAAAAATTATTGCAGGAAGTT
 211 ATTATTCCGAATGGAAGAATAAATAAATATTGGAGGTTAAAGAATGAAAGTTCATATATTGGAAG
                                     EcoR V
 281 GGTATACTGTAGATAAATAAATATTGGAGGATATCGATATGTTTAAATCTAATTATGAAAGAAAATGC
 351 GTTATTCCATTCGTAAATTTAGTGTAGGAGTAGCTAGTGTAGCGGTAGTTGTTCATGGAAGCGT
 421 TGCTCATGCAAGTGAGCTTGTAAGGACGATAGTGTGAAGACTACCGAGGTTGCAGCTAAGCCCTATCCA
 491 AGTATGGCTCAAACAGATCAAGGAGAAATAATTCATCATCCTCGAGAAAACAAAGATGGAAATTC
 561 CTACAACAGACATAAAAAAAGCTGTTGAACCGGTCGAGAAAATAATCTAAAAAATGATGTGGATAACACAATTCTA
 631 TGGAAAACGAGAAACAATTACAACAATGGAAATTTAAACAAACAAATGATTCTGATGCATTATTAGAAT
 701 TCTCATGAACAGAAAAAATGAGTTTAAACAATAATAGACTGTTACACATCAAACATGAAGAAGTTGAGAAAGATAA
 771 TAGAAAATCAATTAACGAAACTAATTAACGAAACTCTGAAACAGTCAGATACGAGAAAGTCTAAGCAATATTGACAAAGAG
                                                        Bgl II
 841 GAAAGCTAAGCAACAGAAAACTCTGAAACTCAAGTTGAAAAATGGCAGAGCAATCACAAAGGAATAAAGATT
 911 CTTAATCATCAAAAAGTCAAGTTGAAAAATGGCAGAGCAATCACAAAGGAATCAAAATGAAGATAAAGATT
 981 CTATGCTGAAAAAATCGAAGATATTCGTAAACAAGCTCAACAAGCAGATAAAAAAGAAGATGCCGAAGT
```

Figure 6A

```
1051  AAAGGTTCGTGAAGAACTAGGTAAACTCTTTAGTTCAACTAAAGCTGGTCTCTGGATCAAGAGAAATTCAAGAG
1121  CATGTGAAGAAAGAAACGAGTAGTGAGGAAAATACTCAGAAGTTGATGAACACTATGCTAATAGCCTTC
1191  AGAACCTTGCTCAAAAATCTCTTGAAGAACTAGATAAGGCAACTACCAATGAACAAGCTACACAAGTTAA
1261  AAATCAATTCTTAGAAACGCTCAAAAGCTCAAAAGAAATACAACCTCTTATCAAAGAAACGAATGTGAAA
1331  TTGTATAAGGCTATGAGTGAGAGCTTGGAGCAGGTTGAGAAGAATTAAAACATAATTCGGAAGCTAATT
1401  TAGAAGATTTGGTTGCGAAATCTAAAGAATCGTAAAGAGAATACGAAGGAAAACTTAATCAATCTAAAAA
1471  TCTTCCAGAATTAAAGCAACTAGAAGAAGCTCATTAGAAGTTGAAACAAGTTGTGGAGGATTTTAGA
1541  AAAAAATTTAAAACGTCAGAGCAAGTGACACCAAAAAAACGTCAAACGAGATTAGCTGCTAATGAAA
1611  ATAATCAACAAAGATTGAGTTAAACAGTTTCACCAGAGAATATCACTGTATATGAAGGTGAAGACGTGAA
1681  ATTTACAGTCACAGCTAAAAGTGATTCGAAGACGACGTTGGACTTCAGTGATCTTTTAACAAAATATAAT
1751  CCGTCTGTATCAGATAGAATTAACACGGATAATCATAAGATTGCCGAAATCA
1821  CTATCAAGAATTTGAAGCTAAATGAAAGTCAAAACAGTGACTCTAAAAGCTAAAGATGATTCTGGCAATGT
1891  AGTTGAAAAAACATTCACTATTACAGTGCAAAAGAAAGAGGAGAAACAAGTTCCTAAAACACCAGAGCAG
```

Figure 6B

```
1961  AAAGATTCTAAAACGGAAGAAAAGGTTCCTCAAGAACCAAATCAAATGACAAGAATCAATTACAAGAGT
2031  TGATTAAATCAGCTCAACAAGAACTGGAAAAGTTAGAAAAGCAATAAAAGAATTAATGGAGCAACCAGA
2101  GATTCCATCCAATCCAGAGTATGGTTATTCAAAAATCTATTTGGGAGTCACAAAAGAGCCTATCCAGGAA
2171  GCCATAACAAGTTTTAAGAAGATTATTGGTGATTCATCTTCAAAATACTACACAGAGCACTATTTAACA
2241  AATATAAATCTGATTTTATGAATTATCAACTTCATGCACAAAATGGAGATGCTGACTAGAAAAGTGGTTCA
2311  GTATATGAACAAATATCCTGATAATGCAGAAATTAAAAAGATATTTGAGTCAGATATGAAGAGAACGAAA
2381  GAAGATAATTACGGAAGTTTAGAAAATGATGCTTTGAAAGGCTATTTTGAGAAATATTTCCTTACACCAT
2451  TTAATAAAATTAAGCAGATTGTAGATGATTTGGATAAAAAAGTAGAACAAGATCAGCCAGCACCAATTCC
2521  GGAAAATTCAGAAATGGATCAGGCTAAGGAAAAGGCTAAGATTGCTGTATCGAAGTATATGAGTAAGGTT
                                                  Pst I
2591  TTAGATGGAGTTCATCAACATCTGCAG
```

Figure 6C

```
              |--------signal sequence--------|
pELF26    1   MFKSNYERKM RYSIRKFSVG VASVAVASLF MGSVAHASEL
pELF26   41   VKDDSVKTTE VAAKPYPSMA QTDQGNNSSS SELETTKMEI
pELF26   81   PTTDIKKAVE PVEKTAGETS ATDTGKREKQ LQQWKNNLKN
pELF26  121   DVDNTILSHE QKNEFKTKID ETNDSDALLE LENQFNETNR
pELF26  161   LLHIKQHEEV EKDKKAKQQK TLKQSDTKVD LSNIDKELNH
pELF26  201   QKSQVEKMAE QKGITNEDKD SMLKKIEDIR KQAQQADKKE
pELF26  241   DAEVKVREEL GKLFSSTKAG LDQEIQEHVK KETSSEENTQ
pELF26  281   KVDEHYANSL QNLAQKSLEE LDKATTNEQA TQVKNQFLEN
pELF26  321   AQKLKEIQPL IKETNVKLYK AMSESLEQVE KELKHNSEAN
pELF26  361   LEDLVAKSKE IVREYEGKLN QSKNLPELKQ LEEEAHz
```

FIGURE 7

GENE AND METHOD FOR PRODUCTION OF AN IGA BINDING PROTEIN

This is a division of application Ser. No. 08/108,828, filed Aug. 18, 1993, now U.S. Pat. No. 5,413,918, which is a continuation of application Ser. No. 07/677,209, filed Mar. 29, 1991, now abandoned.

BACKGROUND OF THE INVENTION

The ability of certain bacterial surface molecules to react selectively with constant regions of many classes and subclasses of IgG molecules from mammalian species has made these Fc-binding proteins of enormous value as immunochemical reagents. These binding proteins can be labeled to high specific activity or immobilized without loss of functional binding and can be used to detect and quantify antigens, fluid phase antibody, and antigen-antibody complexes. The utility of these reagents has been demonstrated by the large number of procedures developed using staphylococcal protein A and streptococcal protein G as tracers and immunoadsorbants for antibodies of the IgG isotype.

IgA is a class of antibody which is related to immunity against infections with bacteria and viruses at mucosal surfaces. It is present in virtually all mammalian secretions. Like other human antibodies, IgA is comprised of heavy and light chains, and is characterized by a constant fraction, Fc, and a variable fraction, Fab. The IgA antibody, like all antibodies, is produced by the lymphocytes of the immune system. To date, the availability of reagents that react selectively with antibodies of the IgA isotype, without interfering with the ability of the antibody molecule to bind to its cognate antigen has been extremely limited. For example, the IgA binding potential of the lectin jacalin is very limited because of its failure to react with both human IgA subclasses and by its non-specific interaction with non-IgA serum proteins (Bunn-Moreno, M. M., A. Campos-Neto [1981] J. Immunol. 127:427–429; Kondoh, H., K. Kobayashi, K. Hagiwara, T. Kajii [1986] J. Immunol. Methods 88:171–173).

Group B streptococci (GBS) are a class of microorganisms which has been extensively studied and classified. GBS are being increasingly recognized as important human pathogens. In addition to causing meningitis, bacteremia, endocarditis, bronchopneumonia, arthritis, peritonitis, wound infections, abscesses, and urinary tract infections in adults, as many as 80% of group B infections occur in neonates (Jelinkova, J. [1977] Current Topics in Microbiology and Immunology 76:127–165). Approximately 30% of pregnant women have been reported to be colonized by GBS. Despite this high carriage rate, neonatal infection occurs with an incidence of only 0.5%, resulting in over 12,000 deaths annually (Lim, D. V., Morales, W. J., Walsh, A. F., and Kazanis, D. [1986] J. Clin. Micro. 23:489–492). Predisposing factors to development of disease are premature birth, prolonged rupture of membranes, overt maternal infection, and deficiency of type specific antibody (Boyer, K. M. and Gotoff, S. P. [1986] New England J. Med. 314:1665–1669). It has now been discovered that certain of these streptococci, generally of the Ib or Ic serotype, will bind IgA.

Bacterial proteins with affinity for Ig classes other than IgG would be of considerable value as immunological tools. It is known that certain streptococcal strains bind IgA (Christensen and Oxelius [1975] Acta Path. Microbial. Scand. Sect. C, 83:184), and isolation of an IgA-binding protein from group B streptococci has even been reported (Russell-Jones et al. [1984] J. Exp. Med. 160:1467). See also U.S. Pat. No. 4,757,134. Western blot analysis of proteins extracted from these strains by treatment with detergent indicated that it may in fact be the β antigen component of the c protein marker complex which has the ability to bind to IgA (Russell-Jones, G. J. and Gotschlich, E. C. [1984] J. Exp. Med. 160:1476–1484). However, the extraction method used by this group—boiling of bacteria in 2% SDS—is not satisfactory for isolation of sufficient amounts of the protein, and the harshness of the procedure is likely to damage the protein. The protein is reported to have a molecular weight of 130 kDa.

In 1987 Cleat and Timmis reported that they had cloned a gene which codes for GBS beta antigen with ability to bind IgA (Cleat, P. H., K. N. Timmis [1987] Infect. Immun. 55:1151–1155). No nucleotide sequence has been reported for the DNA encoding the beta antigen. Recently, studies by Brady and Boyle have indicated that there are various forms of the beta antigen (Brady, L. J., M. D. P. Boyle [1989] Infect. Immun. 57:1573–1581). It was determined that there is a high molecular weight form bound to the surface of bacteria which binds to IgA. In addition, there are secreted proteins that exist in two forms, an IgA binding form and a non-IgA binding form.

In EPC patent application 87850160.0, an IgA-binding protein isolated from *Streptococcus pyogenes* strain AW 43 is described. EPC application 0 367 890 concerns a similar protein with similar binding characteristics but with a different N-terminal sequence. The proteins described in these European patent applications have been isolated from group A streptococci. It has been reported that the receptors obtained from group B streptococci are antigenically unrelated to the IgA receptor from group A streptococci (Lindahl, G. et al. [1990] Eur. J. Immunol. 20:2241–2247).

The subject invention pertains to the cloning and sequencing of a gene which codes for an approximately 45 kDa recombinant protein which binds with IgA.

BRIEF SUMMARY OF THE INVENTION

Described here is a novel process for producing high quantities of an essentially pure IgA binding protein. This process utilizes a novel gene which codes for the IgA binding protein. For brevity, this protein can be referred to as FcRA or recombinant FcRA.

According to the process of the subject invention, microorganisms which have been transformed with the gene coding for the FcRA produce and secrete large quantities of the recombinant protein. Specifically, according to the subject invention, a suitable host can be transformed with DNA comprising the 2.6 kb nucleotide sequence shown in SEQ ID NO. 1. This sequence codes for the IgA binding protein of approximately 45,000 daltons designated FcRA, whose amino acid sequence is shown in SEQ ID NO. 2.

A suitable host may also be transformed with fragments of the novel DNA sequence if it is desired to express only a portion of the IgA binding protein. Furthermore, certain fragments of the novel gene may be combined with regions from genes coding for other proteins to express advantageous hybrid proteins.

The recombinant protein of the subject invention can be used in a variety of assays. Its utility in these assays is enhanced because of its high purity and enhanced specificity compared to wild-type protein produced and recovered from non-recombinant wild-type microbes. The IgA binding protein of the subject invention can be produced for use in radioimmunoassays, enzyme-linked immunoassays, immunoelectronmicroscopy, immunofluorescence, and following immobilization for the purification of different IgA classes and subclasses. When immobilized in a microtiter plate or when biotinlyated FcRA can be used to interact selectively with and facilitate quantitation of human IgA immunoglobulins. FcRA demonstrates remarkable selectivity for IgA, failing to react with any of the human IgG subclasses or with any component present in IgA deficient serum or human cord blood. This high degree of selectivity coupled with its reactivity with both human IgA subclasses, $IgA_1$, and $IgA_2$, demonstrates that this reagent is highly advantageous for procedures involving the isolation and quantification of human IgA. FcRA binds human secretory IgA especially effectively once immobilized on a nitrocellulose membrane, a microtiter plate, or any other appropriate inert support.

BRIEF DESCRIPTION OF THE SEQUENCES

Figure 1:
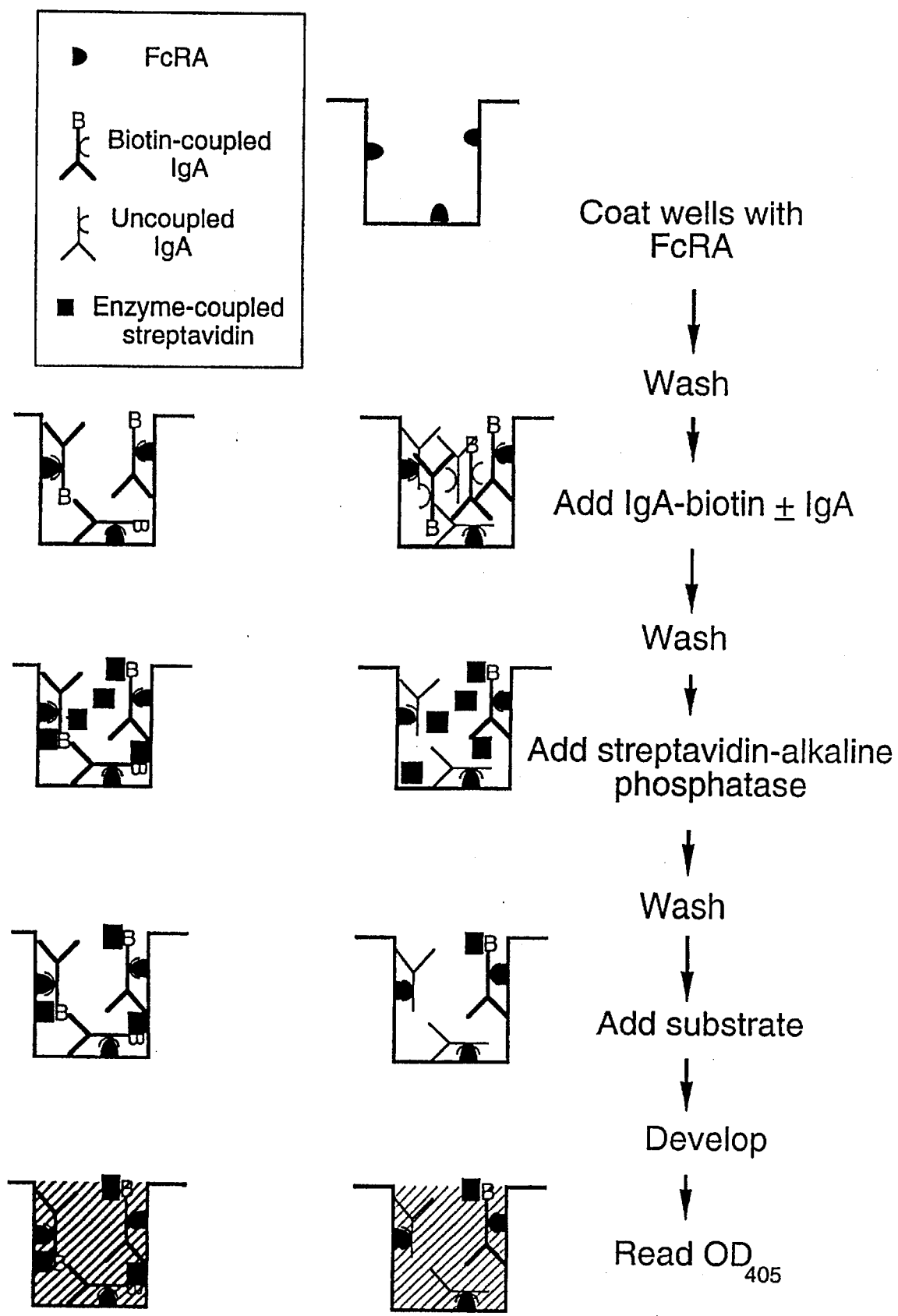
FIG. 1 is a scheme for competitive inhibition ELISA for fluid phase human IgA using biotinylated-IgA as tracer.

FIG. 6 (SEQ ID NO. 1) is the DNA sequence encoding the IgA binding protein of the subject invention.

FIG. 7 (SEQ IS NO. 2) is the predicted amino acid sequence of the novel IgA binding protein.

DETAILED DISCLOSURE OF THE INVENTION

This invention provides a novel recombinant protein and a novel gene and methods for producing this protein. The novel recombinant protein, and subfragments thereof, have affinity for immunoglobulin A (IgA) and can be used in a variety of assays, kits, and pharmaceutical compositions.

One aspect of the subject invention is a gene coding for the recombinant IgA binding protein. The nucleotide sequence of this gene is shown in SEQ ID NO. 1. SEQ ID NO. 2 shows the deduced amino acid sequence of the recombinant protein encoded by the gene shown in SEQ ID NO. 1.

The invention further concerns a recombinant polynucleotide sequence comprising a vector in which a DNA sequence coding for the subject recombinant protein, or a fragment thereof, expressible in a suitable host has been inserted. Thus, said vector encodes the novel IgA binding protein and/or a fragment of this protein with substantially the same binding properties to immunoglobulin A. Specifically, the vector may be chosen from plasmids, phage DNA, or derivates or fragments thereof, or combinations of plasmids and phage DNA and yeast plasmids.

The invention also concerns a host infected, transformed, or transfected with a recombinant DNA molecule comprising a vector in which a DNA sequence coding for the desired protein, or fragment thereof, expressible in a suitable host has been inserted. The inserted DNA is characterized in that the DNA sequence codes for the recombinant IgA binding protein and/or a fragment of this protein with substantially the same binding properties to immunoglobulin A. Among the many suitable hosts that can be infected, transformed, or transfected with the recombinant DNA molecule according to the invention and thereby express this protein or fragments thereof are gram positive or negative bacteria such as *E. coli, Bacillus subtilis*, insect cells, and yeast cells.

The various methods employed in the preparation of the plasmids and transformation of host organisms are well known in the art. These procedures are all described in Maniatis, T., E. F. Fritsch, and J. Sambrook (1982) *Molecular Cloning: A Laboratory Manual*, Cold Spring Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, e.g., *E. coli* cells, prepare plasmid DNA, electrophorese proteins, and sequence DNA.

An *E. coli* which has been transformed with plasmid pELF26 comprising the gene coding for the IgA binding protein has been deposited in the permanent collection of the American Type Culture Collection (ATCC), 12301 Parklawn Drive, Rockville, Md. 20852 U.S.A. on Mar. 5, 1991 and was assigned the accession number ATCC 68553.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The DNA sequence of the subject invention can be most readily obtained by a person skilled in the art by isolating said DNA from ATCC 68553 using methods which are well known to those skilled in the art. The nucleotide sequences disclosed herein can also be prepared by a "gene machine" by procedures well known in the art. This is possible because of the disclosure of the nucleotide sequence.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |
| Termination signal | TGA | | |

Key: Each 3-letter deoxynucleotide triplet corresponds to a trinucleotide of mRNA, having a 5 -end on the left and a 3 -end on the fight. All DNA sequences given herein are those of the strand whose sequence corresponds to the mRNA sequence, with thymine substituted for uracil. The letters stand for the purine or pyrimidine bases forming the deoxynueleotide sequence.

A=adenine

G=guanine

C=cytosine

T=thymine

X=T or C if Y is A or G

X=C if Y is C or T

Y=A, G, C or T if X is C

Y=A or G if X is T

W=C or A if Z is A or G

W=C if Z is C or T

Z=A, G, C or T if W is C

Z=A or G if W is A

QR=TC if S is A, G, C or T; alternatively QR=AG if S is T or C

J=A or G

K=T or C

L=A, T, C or G

M=A, C or T

The above shows that the amino acid sequences of the recombinant IgA binding proteins, and fragments thereof, of the subject invention can be prepared by nucleotide sequences other that which is shown in SEQ ID NO. 1. Functionally equivalent nucleotide sequences encoding the novel amino acid sequences of these proteins and fragments can be prepared by known synthetic procedures. Accordingly, the subject invention includes such functionally equivalent nucleotide sequences.

Thus the scope of the subject invention includes not only the specific nucleotide sequences depicted herein, but also all equivalent nucleotide sequences coding for molecules with substantially the same antigenic, immunogenic, or therapeutic activity.

Further, the scope of the subject invention is intended to cover not only the specific amino acid sequences disclosed, but also similar sequences of proteins or protein fragments having comparable biological activity.

The term "equivalent" is being used in its ordinary patent usage here as denoting a nucleotide sequence which performs substantially as the nucleotide sequence identified herein to produce molecules with substantially the same antigenic, immunogenic, or therapeutic activity in essentially the same kind of hosts. Thus, equivalent nucleotide sequences may code for the same amino acids and/or they may have a high degree of homology such that the amino acids which are coded for have the same biochemical properties as FcRA. The homology may be, for example, 90% or more, or sufficient so that the "equivalent" nucleotide sequence hybridizes to the cDNA for the sequence in SEQ ID NO. 1. Equivalency of amino acid sequences can also be measured in terms of homology and equivalency of function. Within this definition of "equivalents" are subfragments which have equivalent activity.

Utilizing the teachings of the subject invention, the novel DNA sequence, or an equivalent sequence, that codes for the IgA binding proteins thereof can also be isolated from appropriate GBS. The streptococcus cell wall is preferably made fragile and lysed with enzymes, after which the DNA is purified by phenol extraction and density gradient centrifugation. The streptococcus strains are cultivated in a rich medium, preferably in Todd-Hewitt broth (oxoid). The cell wall can be made fragile by adding cysteine, threonine, and glycine to the culture. The bacteria are lysed by the addition of enzymes attacking the peptidoglycan layer (preferably mutanolysin), followed by sodium dodecyl sulfate (SDS). The DNA is purified by phenol extraction and density gradient centrifugation. The streptococcal DNA can be treated with a restriction enzyme to yield fragments that can be ligated to a suitable vector. The vector with inserted streptococcal DNA can then be used to infect, transform, or transfect a host cell. Production of protein can be tested. When bacteriophage lambda is the vector, this can be done by covering plates with plaques with a nitrocellulose membrane, which is then exposed to radioactive IgA or to IgA followed by peroxidase conjugated anti-IgA. Positive reacting clones are collected. Phage clones giving a positive signal contain the protein coding DNA, which can be cut out with restriction enzymes.

The DNA sequence that codes for a protein or a peptide with IgA-binding activity could be any fragment of this insert or any similar nucleotide sequence that codes for and expresses such a protein or peptide or fragments thereof.

The invention further concerns a process for preparing the recombinant FcRA protein and subfragments thereof with IgA binding activity. It is well within the skill of those in the genetic engineering art to use the nucleotide sequences disclosed herein to produce the novel IgA binding proteins via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, IL-1, IL-2, and the like. Similar procedures, or obvious modifications thereof, can be employed to prepare the proteins or fragments of the subject invention by microbial means or tissue-culture technology in accord with the subject invention.

For example, *E. coli* may be infected with phage lambda containing the protein coding DNA sequence and, after lysis, the lysate liquid can be separated from debris and purified by affinity chromatography with a ligand that has affinity for this protein. The ligand is preferably IgA (serum IgA, secretory IgA, $IgA_1$, or $IgA_2$). *E. coli* can be any strain, and it is grown in broth, preferably LB broth. Preferably, protease inhibitors such as benzamidinechloride are added before the liquid lysate is separated.

The protein or subfragments thereof can be used as a reagent for binding, separation, and identification of immunoglobulin A. Since IgA is the predominant antibody in mucous secretions, IgA-binding proteins are of considerable potential interest for the analysis of this important line of host defense.

Immunochemical assays employing the recombinant proteins, or fragments thereof, of the subject invention can take a variety of forms. One preferred type is a liquid phase assay wherein the protein and the sample to be tested are mixed and allowed to form complexes in solution which can then be detected by a variety of methods.

Another application using the recombinant protein of the subject invention is a solid phase immunometric assay. In solid phase assays, an IgA binding protein or peptide of the subject invention can be immobilized on a solid phase to form an antigen-immunoadsorbent. The immunoadsorbent is incubated with the sample to be tested. After an appropriate incubation period, the immunoadsorbent is separated from the sample, and labeled anti-(human IgA) antibody is used to detect IgA bound to the immunoadsorbent. Labeled IgA binding protein could also be used to detect the bound antibody.

The immunoadsorbent can be prepared by adsorbing or coupling a purified IgA binding protein or fragment to a solid phase. Various solid phases can be used, such as beads formed of glass, polystyrene, polypropylene, dextran or other material. Other suitable solid phases include tubes or plates formed from or coated with these materials.

The novel recombinant protein of the subject invention can also be labeled and used to detect IgA which may be bound to a particular antigen in an assay as described above.

The recombinant FcRA protein can also be used for absorption of immunoglobulin A from various biological specimens, such as the blood of patients with autoimmune disease. Thus, the invention also concerns a pharmaceutical composition containing the protein or subfragments thereof as active ingredients, possibly together with pharmaceutically acceptable adjuvants and excipients.

For any of the assays of the subject invention, labeling of the IgA, anti-(human IgA) antibody, or IgA binding protein can be accomplished by any one of a number of means which are well known to those skilled in the art. These means include, but are not limited to, radiolabeling, enzyme-tagging, and fluorescent labels. In many of the examples which follow, biotinylation was used to label the entities, but this form of labeling is only illustrative of the types which could be utilized.

For convenience and standardization, reagents for the performance of immunometric assays can be assembled in assay kits. A kit for screening blood can include, for example, one or more of the following separately compartmentalized components:

(a) an immunoadsorbent, e.g., a polystyrene bead or other solid support coated with a recombinant IgA binding protein or peptide;

(b) a diluent for the serum or plasma sample, e.g. normal human serum or plasma; and (c) an anti-(human IgA) antibody, e.g., goat anti-(human IgA) antibody in buffered, aqueous solution containing about 1% goat serum or plasma.

Positive and negative controls could also be included in the kit.

Materials and Methods

Protein Reagents. Isolated whole human serum and secretory IgA was purchased from Organon Teknika-Cappel (Malvern, Pa.) and Sigma Chemicals (St. Louis, Mo.) respectively. Human IgA and IgG subclass reagents were supplied by the World Health Organization Immunoglobulin Subclass Committee. Human serum containing known amounts of IgA was obtained from Beckman Instruments (Brea, Calif.). Wild-type FcRA and biotinylated FcRA (FcRA-biotin) were obtained from Blake Laboratories (Cambridge, Mass.).

Biotinylation of Human IgA. Human serum IgA, FcRA (or rFcRA) was biotinylated by standard procedures (Fuccillo, D. A. [1985] Biotechniques 3:494–501). The protein to be biotinylated was dialyzed into 0.1M carbonate, pH 9.5, and the resulting solution was adjusted to a concentration of 2 mg/ml. One-tenth volume of biotin-N-hydroxysuccinimide (NHS-biotin), 22 mg/ml in dimethyl sulfoxide, was added and the reaction allowed to proceed 4 hours a ambient temperature. The proteins were separated from the unreacted NHS-biotin by passage over a desalting column, PD-10 (Pharmacia, Piscataway, N.J.), equilibrated in 10 mM phosphate buffered saline, pH 7.4 (PBS).

Direct Binding ELISA. FcRA can be coated onto the wells of flat-bottom polystyrene microtiter plates by adding 100 µl aliquots of various dilution of the protein in 0.1M carbonate buffer, pH 9.6, to the webs and incubating the plates overnight at ambient temperature in a humidified chamber. The wells can be washed 3 times with 20 mM Tris buffered saline (pH 7.5) containing 0.05% Tween-20 and 0.02% $NaN_3$ (TBST). The plates may then be stored at 4 C in a humidified chamber. Unbound reactive sites on the polystyrene can be blocked by washing the wells with 200 µl of TBST containing 0.1% gelatin (Difco, Detroit, Mich.) (TBSTG). IgA-biotin diluted in TBST can be added to the wells (100 µl/well) and allowed to react for 1 hour at ambient temperature. The wells can be washed 6 times with TBST containing 1 mM EDTA (200 µl/well). The amount of biotin remaining in the wells can be determined by addition of streptavidin-alkaline phosphatase (SA-AP) (BioRad, Fremont, Calif.) diluted 1:3000 in TBST, incubation for 1 hour at ambient temperature, followed by washing the wells 6 times with Tris buffered saline (pH 7.5) containing 10 mM $MgCl_2$, and the addition of 100 µl of a freshly prepared chromogenic substrate. The chromogenic substrate solution for this assay may be 1 mg/ml p-nitrophenyl phosphate in 1.0M diethanolamine-HCl, pH 9.8, containing 0.5 mM $MgCl_2$. The amount of substrate cleaved in the wells can be determined by reading the $OD_{405}$ in all ELISA plate reader.

Competitive Binding ELISA. Wells of polystyrene microtiter plates can be coated with target protein (either FcRA, human serum IgA, or secretory IgA) diluted in 0.1M carbonate buffer, pH 9.6, and blocked as described previously. 50 µl aliquots of dilutions of sample solutions in TBST can be added to the wells followed by addition of 50 µl of the biotinylated tracer reagent (i.e., IgA-biotin or rFcRA-biotin). The reactants can be incubated for 1 hour at ambient temperature and unbound material removed by washing the wells 6 times in TBST containing 10 mM EDTA. The amount of biotin remaining associated with the wells can be determined by probing with SA-AP, followed by washing, incubation with chromogenic substrate, and measuring the $OD_{405}$ of the wells as described previously. Inhibition of binding of the biotinylated tracer by various dilutions of the fluid phase competitor can be calculated by comparing the enzyme activity in the presence or the absence of the sample.

Direct Binding Assays on Nitrocellulose Membranes. Samples can be diluted in PBS and 50 µl can be applied to a nitrocellulose membrane in a dot blot suction manifold (Bio-Rad, Fremont, Calif.). The samples can be allowed to interact with the membrane for 20 minutes at ambient temperature and unbound material removed by washing the wells extensively with PBS. The membrane can be removed from the apparatus and washed 4 times in 10 mM veronal buffered saline, pH 7.35, containing 0.25% gelatin and 0.05% Tween-20 (VBSTG) with shaking for 10 minutes, at ambient temperature. The membranae can be probed with rFcRA-biotin diluted 1:20,000 in 20 ml VBSTG in a heat sealed plastic pouch for 3 hours with rotation, at ambient temperature. Unbound material can be removed by washing the membrane 4 times in VBSTG with shaking, at ambient temperature. The binding of the rFcRA-biotin can be traced by probing the membrane with streptavidin-alkaline phosphatase (1:3000 in 10 ml VBSTG) in a heat-sealed pouch of 1 hour with rotation at ambient temperature. The membrane can be removed from the bag and washed 4 times in 250 ml Tris buffed saline with Tween-20 (10 mM Tris-HCl, 150 mM NaCl, 0.05% Tween-20, pH 0.80) as described above. The membrane can then be washed once in Tris buffered saline containing $Mg^{++}$ (10 mM Tris-HCl, 140 mM NaCl, 5 mM $MgCl_2$, pH 8.0), blotted dry, immersed in freshly prepared substrate solution and incubated at ambient temperature until it develops to a sufficient intensity (usually 10–30 minutes), and then washed twice in $H_2O$. The enzyme substrate solution can contain 25 ml 100 mM Tris-HCl, 200 mM NaCl, 5 mM MgCl, pH 9.5; 0.25 ml p-nitro blue tetrazolium chloride solution (30 mg/ml in 70%/30% dimethylforamide/water); and 0.25 ml 5-bromo-4-chloro-3-indoly phosphate-toluidine salt solution (15 mg/ml in dimethylforamide).

Following are examples which illustrate procedures, including the best mode, for practicing the invention. These examples should not be construed as limiting. All percentages are by weight and all solvent mixture proportions are by volume unless otherwise noted.

Example 1 - Cloning of the Gene Coding for FcRA

The cloning procedure was carried out utilizing a HindIII digest of chromosomal DNA that had been sized on agarose to identify a 3.2 kb fragment of DNA. This fragment was then inserted into the HindIII site of pUC18 and used to transform E. coli DH5α. Colonies were screened for the production of an IgA binding protein. Using this strategy, a colony was detected which expressed a recombinant IgA binding protein which was not present in E. coli transformed with pUC18 alone. Bacteria from this colony contained a plasmid designated pELF32. This plasmid was demonstrated to contain a gene coding for a 45,000 molecular weight IgA binding protein which could be expressed at high concentrations without induction. The streptococcal insert DNA from pELF32 was subcloned and a HindIII/PstI fragment (approximately 2.6 kilobases) was inserted into pUC18. The resulting plasmid was designated pELF26. Bacteria containing this plasmid expressed an IgA binding protein (approximately 45,000) and has been used for all of the sequencing studies. The streptococcal DNA insert of this subcloned plasmid has the sequence shown in SEQ ID NO. 1.

Example 2 - Direct Binding of IgA-Biotin to Immobilized FcRA

The initial focus of these studies was to develop an assay to detect IgA in the fluid phase. For these studies recombinant FcRA was first immobilized on microtiter plates and biotinylated IgA was used as the tracer molecule in the assay system. Various concentrations of FcRA solution were used to coat the wells of a 96-well polystyrene ELISA plates overnight at ambient temperature. Unbound reactive sites were blocked by incubation with a buffer containing gelatin, TBSTG. The ability of immobilized FcRA to react with human IgA was determined by incubating the immobilized protein with solutions containing various dilutions of biotinylated-IgA. The reactants were incubated for 1 hour at room temperature before removing unbound biotinylated-IgA by washing. The quantity of IgA-biotin remaining associated with the wells was determined by incubation with streptavidin coupled to alkaline phosphatase. The wells were washed 6 times with Tris-buffered saline containing 5 mM $MgCl_2$ and the quantity of immobilized enzyme associated with the microtiter plate was determined by addition of an appropriate chromogenic substrate. The extent of substrate cleavage was determined by measuring the absorbance at 405 nanometers in an ELISA plate reader.

The results of a typical checkerboard analysis demonstrate that the concentration of IgA-biotin associated with the plates was dependent on both the concentration of FcRA used to coat the plate and on the quantity of IgA-biotin tracer added to the wells. From these experiments, condition were selected to develop a competitive binding assay to quantitate IgA in the fluid phase. The conditions chosen were: a coating dilution of FcRA of 1:2000 and the IgA-biotin diluted 1:1000 (approximately 1 μl/ml).

Example 3 - Competitive Inhibition Assay Using Immobilized FcRA and IgA-Biotin

The basic protocol for the competitive binding assay is presented in FIG. 1. The results of assays in which different dilutions of serum IgA, $IgA_1$, $IgA_2$, or secretory IgA were tested revealed that the competitive binding ELISA was sensitive, with approximately 40% inhibition of IgA-biotin binding being achieved upon the addition of approximately 10–20 ng of fluid phase human serum IgA. The inhibition curves obtained with $IgA_1$ and $IgA_2$ were similar and indicated that FcRA could bind to both IgA subclasses with approximately equivalent affinity.

This assay was less sensitive for human secretory IgA with approximately 40% inhibition being achieved upon the addition of 1–2 μg of fluid phase human secretory IgA.

The next series of experiments were designed to test the specificity of the FcRA reagent for IgA. Two series of studies were performed. The first set of experiments were designed to determine whether there was any reactivity with any of the human IgG subclasses. The results revealed no inhibition of IgA-biotin binding to FcRA by any of the human IgG subclass proteins.

These studies of the specificity of FcRA were extended to test the efficiency of binding of IgA to FcRA in complex solutions. For these studies a sample of purified IgA was added to an IgA deficient cord blood sample and the efficiency of detection of IgA in this complex mixture of non-IgA serum proteins was measured using the competitive binding assay outlined in FIG. 1. The results revealed that, within experimental error, the level of IgA detected in the cord blood sample was the same as observed for the purified IgA sample diluted in buffer. These results indicate that the assay is specific for IgA and is not influenced by other proteins present in human serum. Similar results were obtained when IgA deficient human sera were studied.

The competitive binding assay was also used to measure the level of IgA in a series of normal human sera. Levels within the normal range reported for human serum IgA were obtained. Taken together, these results indicate that FcRA immobilized on microtiter plates provides a specific capture reagent for the detection and quantification of IgA in serum.

Example 4 - Use of Biotinylated-FcRA as a Tracer for Human IgA

The next series of experiments were designed to determine whether tracer forms of FcRA could be generated that would enable the detection of mobilized IgA. Biotinylated FcRA (FcRA-biotin) retained its ability to bind IgA as determined in the direct binding assay with various dilutions of whole serum IgA coated on microtiter wells followed by probing the wells with streptavidin conjugated to alkaline phosphatase and using an appropriate chromogenic substrate.

Figure 2:
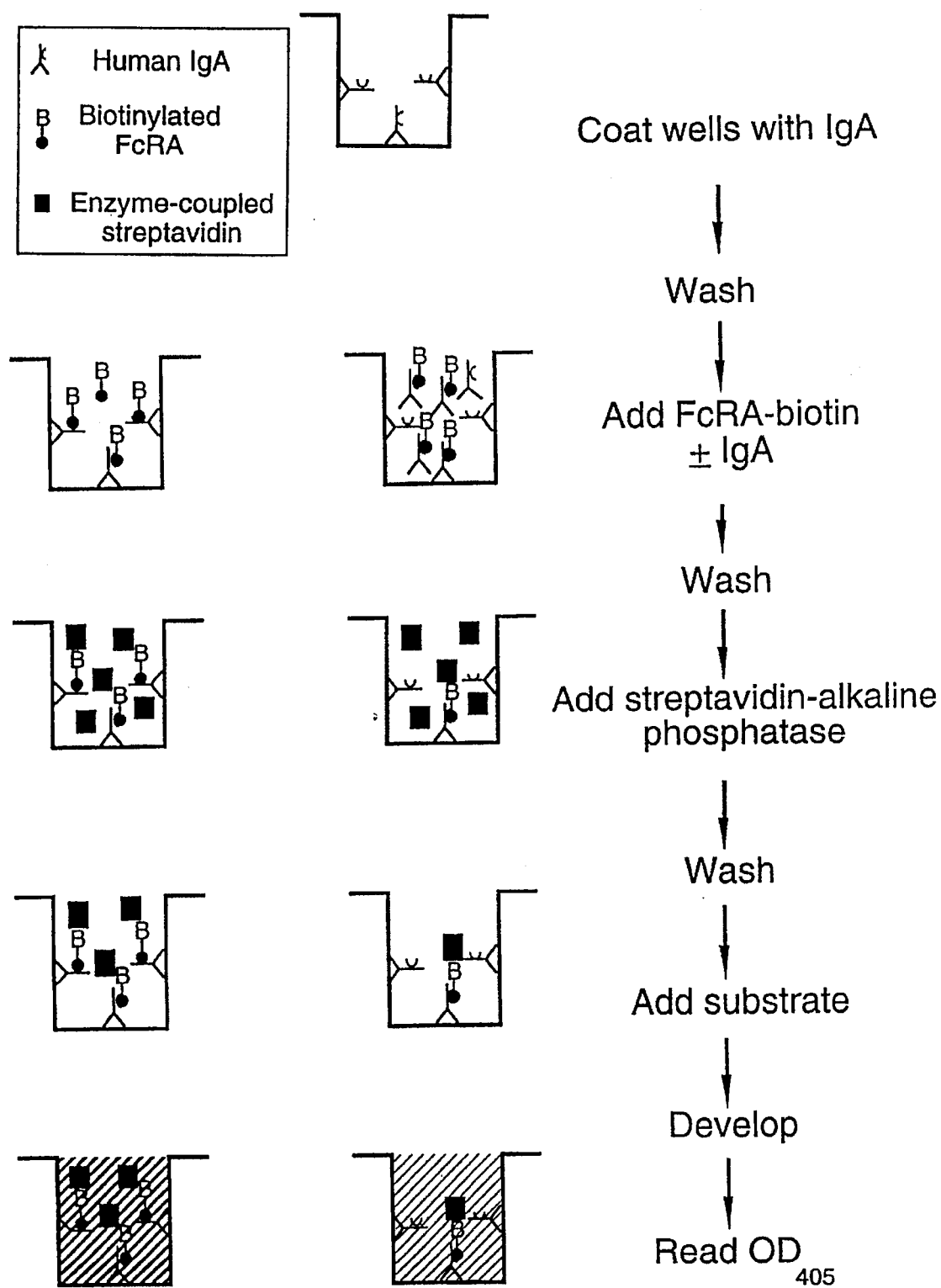
FIG. 2 is a scheme for competitive inhibition ELISA for fluid phase human IgA using biotinylated-FcRA as tracer.

A competitive ELISA assay was developed to determine fluid phase IgA, in which IgA-coated microtiter wells were employed and the FcRA-biotin was used a tracer. The protocol for this assay is summarized in FIG. 2. Optimal concentrations of IgA for coating the wells of the microtiter plates (10 ng/well) and of the FcRA-biotin tracer (12.5 ng/well) to use in this assay were determined from the results of direct binding assays using the procedures described above. Results of a competitive binding assay using serum IgA, secretory IgA, or serum IgA diluted in cord blood as competitors of the interaction of FcRA-biotin with immobilized human serum IgA demonstrate that the FcRA-biotin tracer was effective in detecting serum IgA and this assay was as efficient in the presence of non-IgA serum proteins present in cord blood. Both secretory IgA and serum IgA were detected by the tracer.

Figure 3:
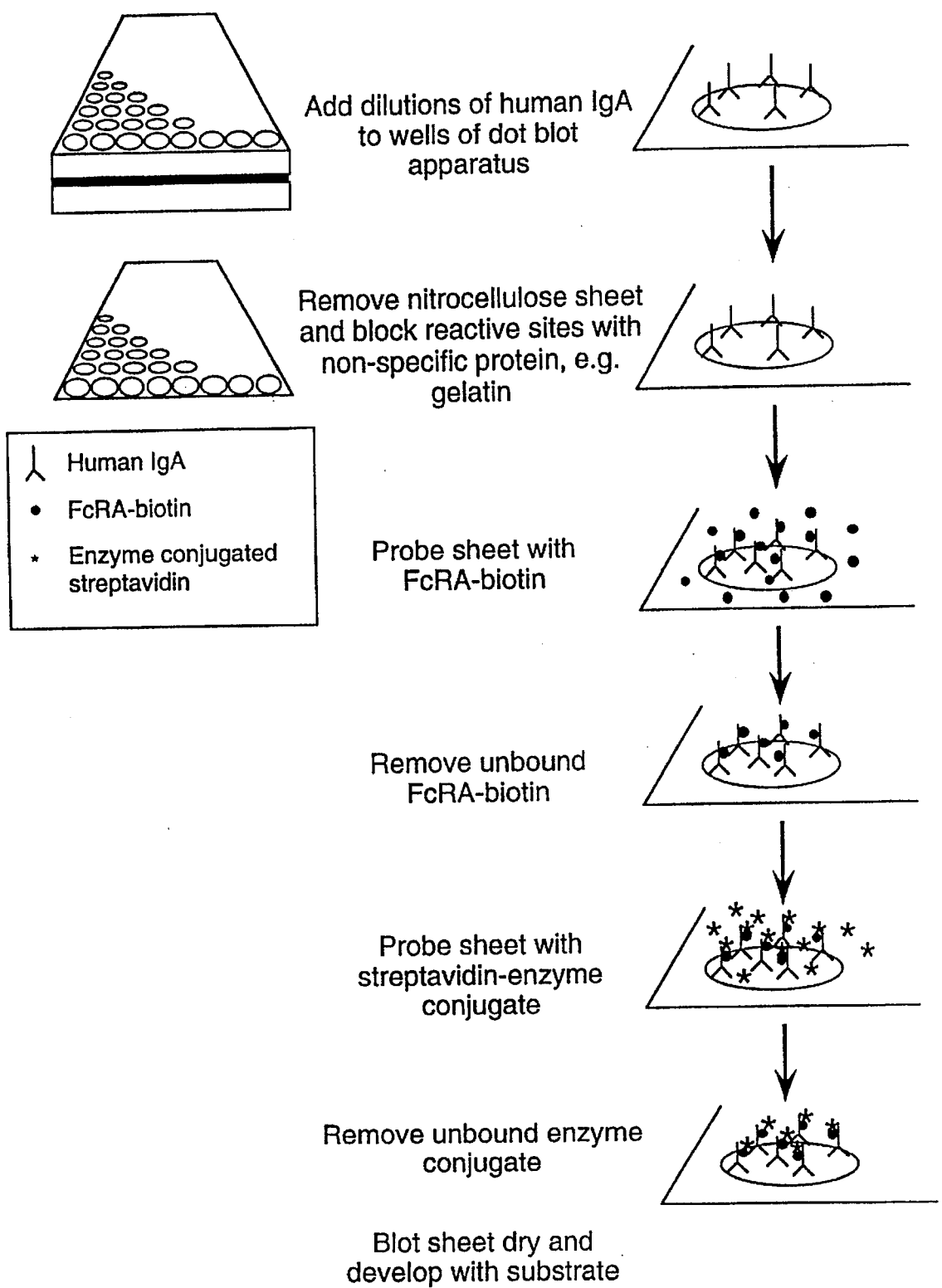
FIG. 3 is a scheme for IgA dot blot using biotinylated-FcRA as tracer.

Example 5 - Use of FcRA-Biotin Tracers to Detect Human IgA Immobilized on Nitrocellulose Membranes In the next series of studies the ability to detect different forms of IgA immobilized on nitrocellulose was determined. The general procedure for these assays is outlined in FIG. 3. In these experiments different concentrations of IgA from various sources were applied to a nitrocellulose membrane in a dot blot apparatus, the membrane was washed, and unreactive sites on the charged membrane blocked by washing with a buffer solution containing gelatin. The blocked membrane was probed with a 1:20,000 dilution (approximately 250 ng/ml) of FcRA-biotin, incubated for 3 hours at room temperature followed by washing to remove the unbound probe. The quantity of FcRA bound to the immobilized IgA was determined by probing with a streptavidin-alkaline phosphatase conjugate and an appropriate chromogenic substrate that, when cleaved, precipitated on the membrane. The result of this assay revealed that both human serum IgA and human secretory IgA were detected. There was no background reactivity detected when IgA deficient cord blood and IgA added to cord blood could be reliably detected using this procedure. These results indicate that the FcRA-biotin tracer was effective at detecting IgA when either immobilized on a plastic surface or immobilized on nitrocellulose.

Example 6 - Binding Regions of FcRA

Figure 4:
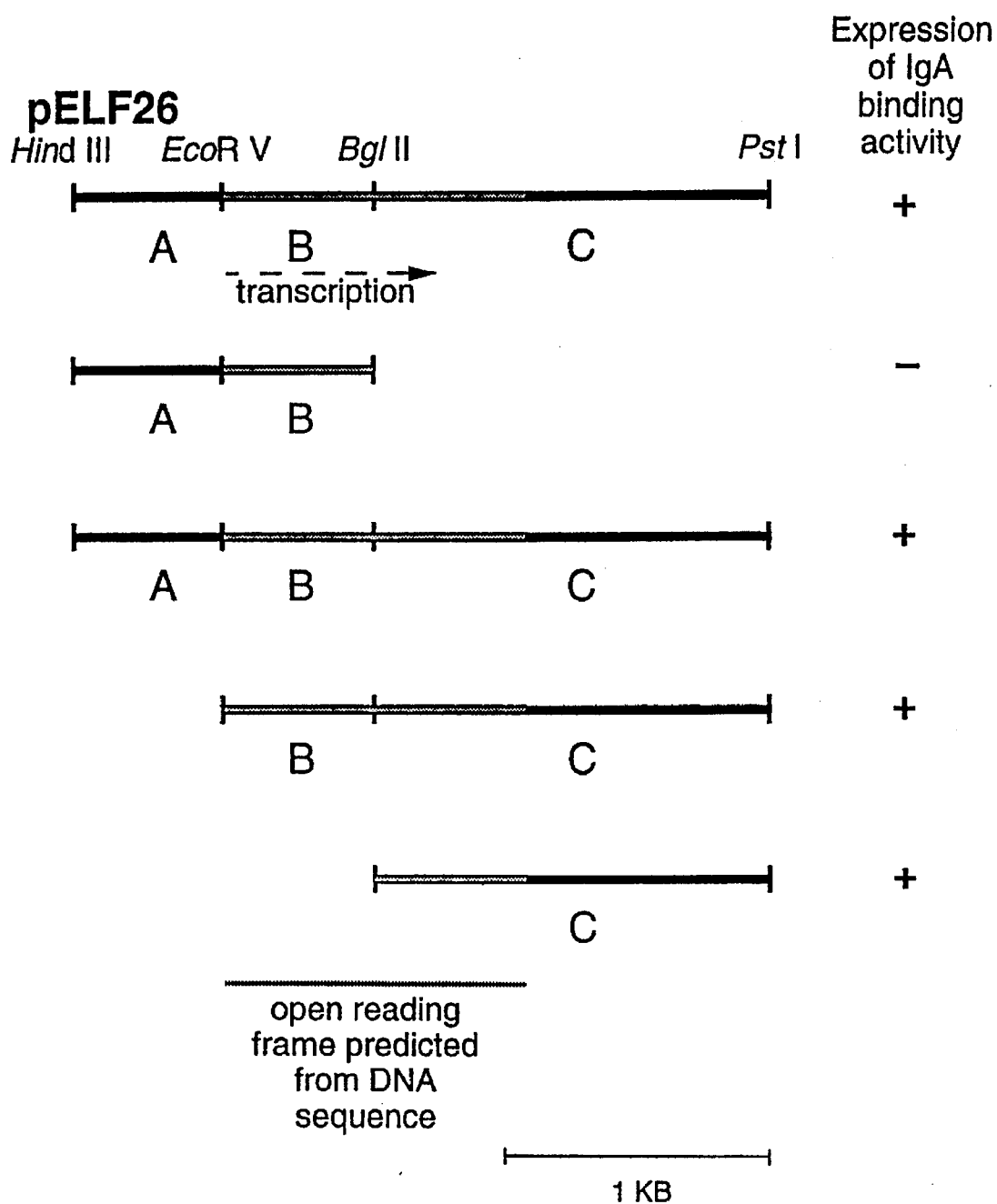
FIG. 4 shows expression of IgA binding proteins by subclones of pELF26. From these results, the IgA binding region of the protein expressed by pELF26 would be encoded in the DNA sequence in the 639 bp at the 5 end of the 'C' region of the gene.
Figure 5:
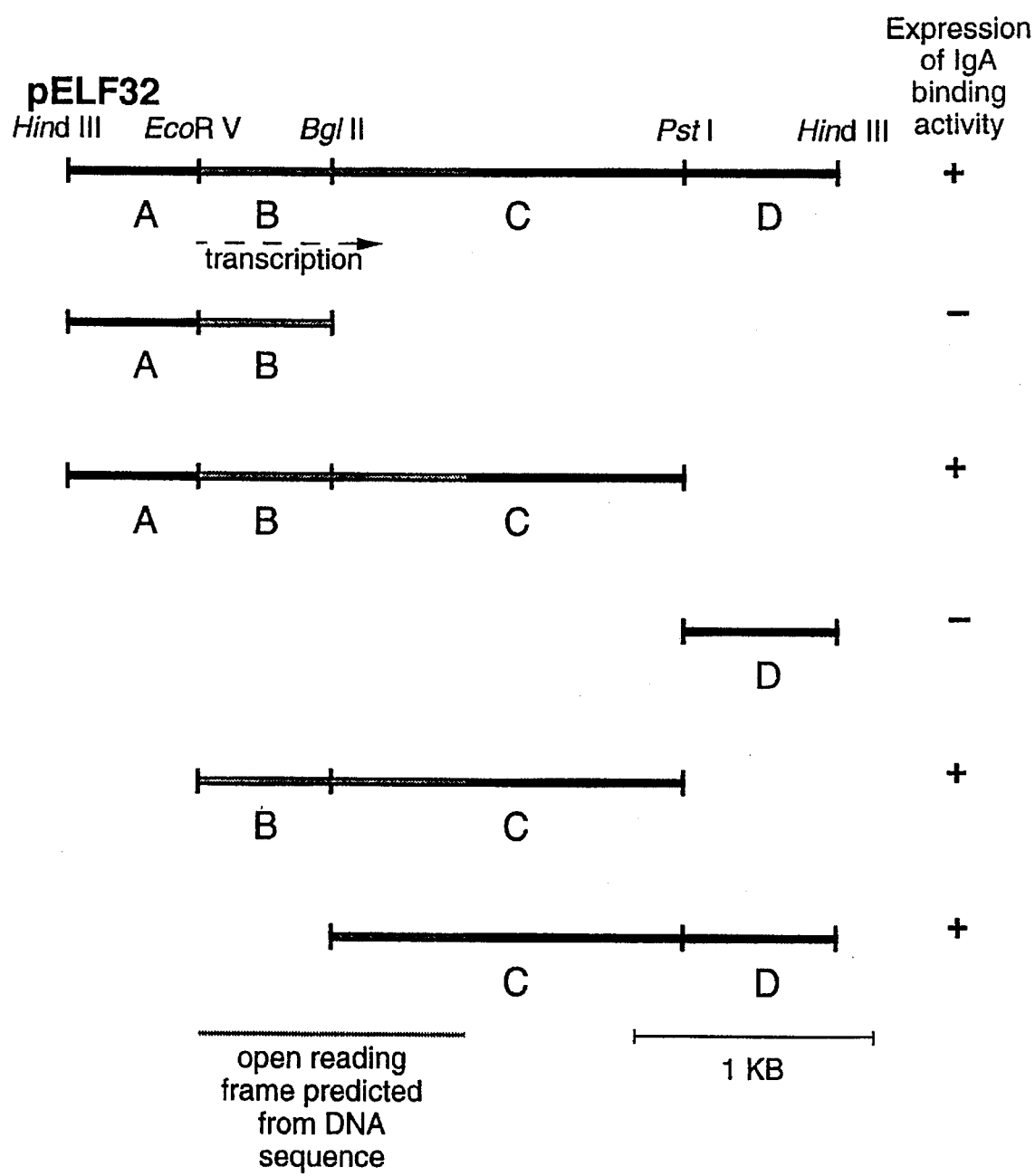
FIG. 5 shows expression of IgA binding proteins by subclones of pELF32.

As discussed above, various fragments of the FcRA protein have been found to have IgA binding activity. It is within the skill of a person trained in this art to utilize the teachings provided herein to identify IgA binding domains of the FcRA molecule. For example, as shown in FIGS. 4 and 5, certain fragments of this protein have been shown to exhibit IgA binding activity. Specifically, amino acid sequences coded by the base sequences between the HindIII and PstI restriction sites (pELF26 and pELF32), EcoRV and PstI restriction sites (pELF26 and pELF32), and between the BglII and HindIII restriction sites (pELF32) have all been found to bind IgA. Conversely, amino acid sequences coded by the bases between HindIII and BglII (pELF26 and pELF32), and PstI and HindIII (pELF32) do not bind IgA. It can be inferred from these results that the IgA binding region of FcRA is within the fragment coded by the bases between the BglII and PstI restriction sites of pELF26 and pELF32. It should be noted that the amino acid sequence shown in SEQ ID NO. 2 is coded for by the nucleotide bases from the codon at positions 320–322 to the codon at positions 1508–1510 in SEQ ID NO. 1. Therefore, particularly advantageous fragments of the gene of the subject invention include the portion from base 320 to base 1510 and, most advantageously, the portion from the BglII site to base 1510.

Example 7 - Modification of FcRA to Increase Effective Affinity

The affinity of the novel IgA binding protein is markedly influenced by the number of repetitive binding domains that are expressed in the molecule. To those skilled in the art of genetic engineering, it is possible to combine coding regions for the IgA binding activity in repetitive sequence to increase the effective avidity of the IgA binding protein. This procedure has been shown for streptococcal protein G to be capable of increasing the affinity of this IgG binding protein from 10- to 60-fold.

Example 8 - Hybrid Proteins

The full length FcRA molecule, or fragments thereof, can be combined with other proteins to produce hybrid proteins having advantageous properties. This is most efficiently accomplished by ligating DNA coding for the relevant portions of the FcRA molecule to DNA coding for the desired portions of other proteins. For example, a hybrid protein can be prepared which has the ability to bind both IgA and IgG. The gene coding for the hybrid protein can be prepared by, for example, ligating the DNA coding for FcRA (or an IgA binding fragment thereof) to DNA coding for an IgG binding domain of protein G or protein A. The IgG binding domains of protein G and protein A are known to those skilled in the art and can be found in the literature. The gene encoding the novel hybrid protein can then be transformed into an appropriate host which expresses the recombinant protein.

A recombinant protein having the capability to bind both IgA and IgG has a number of uses. For example, if it is desired to detect IgM in a serum sample, it is advantageous to remove from that sample other classes of immunoglobulins, i.e., IgA and IgG, before assaying for IgM. The novel hybrid protein of the subject invention can be used to remove both IgG and IgA in a single step.

Example 9 - Insertion of a Cysteine Residue into FcRA

As can be seen from SEQ ID NO. 2, the amino acid sequence of FcRA does not comprise any cysteine residues. The DNA sequence coding for FcRA can be modified by, for example, site directed mutagenesis to insert one or more cysteine residues in a portion of the molecule which will not adversely affect the IgA binding activity of the protein. Most advantageously, only one such cysteine would be inserted. The addition of the cysteine residue facilitates the coupling of the protein to inert supports or other entities. These other entities can include proteins, for example, enzymes or streptavidin. Activated thiol sepharose 4B (Pharmacia Fine Chemicals) is an example of a gel that reacts with reduced sulfhydryl groups to form stable, covalent disulfide bonds. The addition of the cysteine can be accomplished by a variety of means known to those skilled in the art. See, for example, EP 0284368. The exact location of the inserted cysteine within the amino acid sequence can be selected by a person skilled in the art. Advantageously, the cysteine residue will be located outside of the IgA binding regions of the molecule. These binding regions are described in Example 6. The pKa of the sulfhydryl group of a C- or N-terminal cysteine residue is higher than that of an internal cysteine residue, consequently the terminal group is less reactive. Therefore, if the cysteine residue is placed at either end of the FcRA molecule, an additional residue, such as glycine, can also be added to the terminal.

Example 10 - Other Modifications of FcRA

By site directed mutagenesis, it is possible to insert regions of tyrosine residues to facilitate the more effective radiolabeling of the protein by conventional methods. The ability to also insert polylysine tails on the molecule by genetic engineering approaches would also have some benefit for certain modification procedures.

The nucleotide sequence encoding FcRA and modification thereof can also be prepared by a "gene machine" by procedures well known in the art. This is possible because of the disclosure of the nucleotide sequence.

The amino acid sequence of FcRA and modifications thereof can be chemically synthesized by solid phase peptide synthetic techniques such as BOC and FMOC (Merrifield, R. B. [1963] J. Amer. Chem. Soc. 85:2149; Chang, C. and J. Meinhoffer [1978] Int. J. Peptide Protein Res. 11:246).

It should be understood that the examples and embodiments described herein are for illustrative purposes only and that various modifications or changes in light thereof will be suggested to persons skilled in the art and are to be included within the spirit and purview of this application and the scope of the appended claims.

---

I claim:

1. A recombinant polypeptide produced by the process comprising the steps of transforming an appropriate host with a polynucleotide sequence encoding a polypeptide which binds with IgA, wherein said polypeptide is an approximately 40 to 45 kDa protein expressed by a Group B streptococcus, said process further comprising isolating and purifying said recombinant polypeptide expressed by said transformed host.

2. An immunoadsorbent comprising a protein of claim 1 bound to an inert support.

3. A kit comprising a compartment which contains the immunoadsorbent of claim 2.

4. A substantially pure polypeptide comprising an IgA binding domain which consists of amino acids encoded by the polynucleotide sequence from the BglII to PstI restriction sites of pELF26.

5. The polypeptide, according to claim 1, wherein said IgA binding domain consists of amino acids encoded by the polynucleotide sequence between nucleotides 320 and 1510 of SEQ ID NO: 1.

6. The polypeptide, according to claim 4, wherein said IgA binding domain consists of amino acids encoded by the polynucleotide sequence from the BglII site to nucleotide 1510 of SEQ ID NO: 1.

7. A recombinant chimeric protein, comprising an IgA binding domain and an IgG binding domain, wherein said binding domain for IgA is an approximately 40 to 45 kDa protein expressed by a Group B streptococcus.

8. The recombinant protein, according to claim 7, wherein said IgA binding domain consists of amino acids encoded by the polynucleotide sequence from the BglII to PstI restriction sites of pELF26.

9. The recombinant protein, according to claim 7, wherein said IgA binding domain consists of amino acids encoded by the polynucleotide sequence from the BglII site to nucleotide 1510 of SEQ ID NO. 1.

10. The recombinant protein, according to claim 7, wherein said IgA binding domain consists of amino acids encoded by the polynucleotide sequence between nucleotides 320 to 1510 of SEQ ID NO: 1.

* * * * *

UNITED STATES PATENT AND TRADEMARK OFFICE
CERTIFICATE OF CORRECTION

PATENT NO. : 5,644,030
DATED      : July 1, 1997
INVENTOR(S) : Ervin Faulmann

It is certified that error appears in the above-indentified patent and that said Letters Patent is hereby corrected as shown below:

Column 8, line 16: "the webs" should read --the wells--

Column 20, line 60: "according to claim 1" should read --according to claim 4--

Signed and Sealed this

Fourteenth Day of October, 1997

*Attest:*

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2617 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Streptococcus agalactiae
        ( B ) STRAIN: DL471

( v i i ) IMMEDIATE SOURCE:
        ( B ) CLONE: pELF26

( i x ) FEATURE:
        ( A ) NAME/KEY: sig_peptide
        ( B ) LOCATION: 320..430

( i x ) FEATURE:
        ( A ) NAME/KEY: CDS
        ( B ) LOCATION: 320..1510
        ( D ) OTHER INFORMATION: /codon_start= 320
            / function= "binds to Fc region of human IgA"
            / product= "IgA binding protein"
            / number= 1

( i x ) FEATURE:
        ( A ) NAME/KEY: RBS
        ( B ) LOCATION: 307..311

( i x ) FEATURE:
        ( A ) NAME/KEY: protein_bind
        ( B ) LOCATION: 887..1507
        ( C ) IDENTIFICATION METHOD: experimental
        ( D ) OTHER INFORMATION: /bound_moiety= "IgA Fc"
            / evidence= EXPERIMENTAL
            / standard_name= "Human IgA-Fc binding"
            / label= IgA-binding ( x i ) SEQUENCE DESCRIPTION: SEQ ID NO:1:

```
AAGCTTATGC  TTGTCAATAA  TCACAAATTT  GTAGATCACT  TCCTTTTTAG  GACTGTAAAG        60

CATCCTAATT  ACTTTTAAA   TATATTACCA  GAACTAGTTG  GTTTGGCCCT  GGTGAGTCAT       120

GCTTATGTGA  CATTCATCTT  TATTTTTCCT  GTCTATGCGG  TTATTCTTTA  TCAAAGAATA       180

GCAGAGGAAG  AAAAATTATT  GCAGGAAGTT  ATTATTCCGA  ATGGAAGAAT  GAAAGGTTAA       240

AAATAATATA  CCCAATTTAA  TATGCAGTTC  ATATTGGAAG  GGTATACTGT  AGATAAATAA       300

AATATTGGAG  GATATCGAT   ATG  TTT  AAA  TCT  AAT  TAT  GAA  AGA  AAA  ATG  CGT   352
                       Met  Phe  Lys  Ser  Asn  Tyr  Glu  Arg  Lys  Met  Arg
```

```
                          1                    5                              10
TAT  TCC  ATT  CGT  AAA  TTT  AGT  GTA  GGA  GTA  GCT  AGT  GTA  GCG  GTA  GCT      400
Tyr  Ser  Ile  Arg  Lys  Phe  Ser  Val  Gly  Val  Ala  Ser  Val  Ala  Val  Ala
               15                   20                   25

AGT  TTG  TTC  ATG  GGA  AGC  GTT  GCT  CAT  GCA  AGT  GAG  CTT  GTA  AAG  GAC      448
Ser  Leu  Phe  Met  Gly  Ser  Val  Ala  His  Ala  Ser  Glu  Leu  Val  Lys  Asp
               30                   35                   40

GAT  AGT  GTG  AAG  ACT  ACC  GAG  GTT  GCA  GCT  AAG  CCC  TAT  CCA  AGT  ATG      496
Asp  Ser  Val  Lys  Thr  Thr  Glu  Val  Ala  Ala  Lys  Pro  Tyr  Pro  Ser  Met
          45                   50                   55

GCT  CAA  ACA  GAT  CAA  GGA  AAT  AAT  TCA  TCA  TCC  TCG  GAA  CTT  GAG  ACA      544
Ala  Gln  Thr  Asp  Gln  Gly  Asn  Asn  Ser  Ser  Ser  Ser  Glu  Leu  Glu  Thr
60                   65                   70                             75

ACA  AAG  ATG  GAA  ATT  CCT  ACA  ACA  GAC  ATA  AAA  AAA  GCT  GTT  GAA  CCG      592
Thr  Lys  Met  Glu  Ile  Pro  Thr  Thr  Asp  Ile  Lys  Lys  Ala  Val  Glu  Pro
                    80                   85                        90

GTC  GAG  AAA  ACA  GCT  GGG  GAA  ACA  TCT  GCC  ACT  GAT  ACT  GGA  AAA  CGA      640
Val  Glu  Lys  Thr  Ala  Gly  Glu  Thr  Ser  Ala  Thr  Asp  Thr  Gly  Lys  Arg
               95                   100                  105

GAG  AAA  CAA  TTA  CAA  CAA  TGG  AAA  AAT  AAT  CTA  AAA  AAT  GAT  GTG  GAT      688
Glu  Lys  Gln  Leu  Gln  Gln  Trp  Lys  Asn  Asn  Leu  Lys  Asn  Asp  Val  Asp
          110                  115                  120

AAC  ACA  ATT  CTA  TCT  CAT  GAA  CAG  AAA  AAT  GAG  TTT  AAA  ACA  AAA  ATT      736
Asn  Thr  Ile  Leu  Ser  His  Glu  Gln  Lys  Asn  Glu  Phe  Lys  Thr  Lys  Ile
     125                  130                  135

GAT  GAA  ACA  AAT  GAT  TCT  GAT  GCA  TTA  TTA  GAA  TTA  GAA  AAT  CAA  TTT      784
Asp  Glu  Thr  Asn  Asp  Ser  Asp  Ala  Leu  Leu  Glu  Leu  Glu  Asn  Gln  Phe
140                  145                  150                            155

AAC  GAA  ACT  AAT  AGA  CTG  TTA  CAC  ATC  AAA  CAA  CAT  GAA  GAA  GTT  GAG      832
Asn  Glu  Thr  Asn  Arg  Leu  Leu  His  Ile  Lys  Gln  His  Glu  Glu  Val  Glu
               160                  165                  170

AAA  GAT  AAG  AAA  GCT  AAG  CAA  CAG  AAA  ACT  CTG  AAA  CAG  TCA  GAT  ACG      880
Lys  Asp  Lys  Lys  Ala  Lys  Gln  Gln  Lys  Thr  Leu  Lys  Gln  Ser  Asp  Thr
               175                  180                  185

AAA  GTA  GAT  CTA  AGC  AAT  ATT  GAC  AAA  GAG  CTT  AAT  CAT  CAA  AAA  AGT      928
Lys  Val  Asp  Leu  Ser  Asn  Ile  Asp  Lys  Glu  Leu  Asn  His  Gln  Lys  Ser
          190                  195                  200

CAA  GTT  GAA  AAA  ATG  GCA  GAG  CAA  AAG  GGA  ATC  ACA  AAT  GAA  GAT  AAA      976
Gln  Val  Glu  Lys  Met  Ala  Glu  Gln  Lys  Gly  Ile  Thr  Asn  Glu  Asp  Lys
     205                  210                  215

GAT  TCT  ATG  CTG  AAA  AAA  ATC  GAA  GAT  ATT  CGT  AAA  CAA  GCT  CAA  CAA     1024
Asp  Ser  Met  Leu  Lys  Lys  Ile  Glu  Asp  Ile  Arg  Lys  Gln  Ala  Gln  Gln
220                  225                  230                            235

GCA  GAT  AAA  AAA  GAA  GAT  GCC  GAA  GTA  AAG  GTT  CGT  GAA  GAA  CTA  GGT     1072
Ala  Asp  Lys  Lys  Glu  Asp  Ala  Glu  Val  Lys  Val  Arg  Glu  Glu  Leu  Gly
               240                  245                  250

AAA  CTC  TTT  AGT  TCA  ACT  AAA  GCT  GGT  CTG  GAT  CAA  GAA  ATT  CAA  GAG     1120
Lys  Leu  Phe  Ser  Ser  Thr  Lys  Ala  Gly  Leu  Asp  Gln  Glu  Ile  Gln  Glu
               255                  260                  265

CAT  GTG  AAG  AAA  GAA  ACG  AGT  AGT  GAG  GAA  AAT  ACT  CAG  AAA  GTT  GAT     1168
His  Val  Lys  Lys  Glu  Thr  Ser  Ser  Glu  Glu  Asn  Thr  Gln  Lys  Val  Asp
          270                  275                  280

GAA  CAC  TAT  GCT  AAT  AGC  CTT  CAG  AAC  CTT  GCT  CAA  AAA  TCT  CTT  GAA     1216
Glu  His  Tyr  Ala  Asn  Ser  Leu  Gln  Asn  Leu  Ala  Gln  Lys  Ser  Leu  Glu
     285                  290                  295

GAA  CTA  GAT  AAG  GCA  ACT  ACC  AAT  GAA  CAA  GCT  ACA  CAA  GTT  AAA  AAT     1264
Glu  Leu  Asp  Lys  Ala  Thr  Thr  Asn  Glu  Gln  Ala  Thr  Gln  Val  Lys  Asn
300                  305                  310                            315

CAA  TTC  TTA  GAA  AAC  GCT  CAA  AAG  CTC  AAA  GAA  ATA  CAA  CCT  CTT  ATC     1312
Gln  Phe  Leu  Glu  Asn  Ala  Gln  Lys  Leu  Lys  Glu  Ile  Gln  Pro  Leu  Ile
```

```
              320                      325                      330
AAA GAA ACG AAT GTG AAA TTG TAT AAG GCT ATG AGT GAG AGC TTG GAG        1360
Lys Glu Thr Asn Val Lys Leu Tyr Lys Ala Met Ser Glu Ser Leu Glu
            335                      340                  345

CAG GTT GAG AAG GAA TTA AAA CAT AAT TCG GAA GCT AAT TTA GAA GAT        1408
Gln Val Glu Lys Glu Leu Lys His Asn Ser Glu Ala Asn Leu Glu Asp
        350                      355                  360

TTG GTT GCG AAA TCT AAA GAA ATC GTA AGA GAA TAC GAA GGA AAA CTT        1456
Leu Val Ala Lys Ser Lys Glu Ile Val Arg Glu Tyr Glu Gly Lys Leu
        365                  370                      375

AAT CAA TCT AAA AAT CTT CCA GAA TTA AAG CAA CTA GAA GAG GAA GCT        1504
Asn Gln Ser Lys Asn Leu Pro Glu Leu Lys Gln Leu Glu Glu Glu Ala
380                      385                  390                 395

CAT TAGAAGTTGA AACAAGTTGT GGAGGATTTT AGAAAAAAAT TTAAAACGTC             1557
His

AGAGCAAGTG ACACCAAAAA AACGTGTCAA ACGAGATTTA GCTGCTAATG AAAATAATCA      1617

ACAAAAGATT GAGTTAACAG TTTCACCAGA GAATATCACT GTATATGAAG GTGAAGACGT      1677

GAAATTTACA GTCACAGCTA AAAGTGATTC GAAGACGACG TTGGACTTCA GTGATCTTTT      1737

AACAAAATAT AATCCGTCTG TATCAGATAG AATTAGTACA AATTATAAGA CTAACACGGA      1797

TAATCATAAG ATTGCCGAAA TCACTATCAA GAATTTGAAG CTAAATGAAA GTCAAACAGT      1857

GACTCTAAAA GCTAAGATG ATTCTGGCAA TGTAGTTGAA AAAACATTCA CTATTACAGT       1917

GCAAAGAAA GAGGAGAAAC AAGTTCCTAA ACACCAGAG CAGAAAGATT CTAAAACGGA        1977

AGAAAAGGTT CCTCAAGAAC CAAAATCAAA TGACAAGAAT CAATTACAAG AGTTGATTAA      2037

ATCAGCTCAA CAAGAACTGG AAAAGTTAGA AAAAGCAATA AAGAATTAA TGGAGCAACC       2097

AGAGATTCCA TCCAATCCAG AGTATGGTAT TCAAAAATCT ATTTGGGAGT CACAAAAAGA      2157

GCCTATCCAG GAAGCCATAA CAAGTTTTAA GAAGATTATT GGTGATTCAT CTTCAAAATA     2217

CTACACAGAG CACTATTTTA ACAAATATAA ATCTGATTTT ATGAATTATC AACTTCATGC      2277

ACAAATGGAG ATGCTGACTA GAAAAGTGGT TCAGTATATG AACAAATATC CTGATAATGC     2337

AGAAATTAAA AAGATATTTG AGTCAGATAT GAAGAGAACG AAAGAAGATA ATTACGGAAG      2397

TTTAGAAAAT GATGCTTTGA AAGGCTATTT TGAGAAATAT TTCCTTACAC CATTTAATAA      2457

AATTAAGCAG ATTGTAGATG ATTTGGATAA AAAAGTAGAA CAAGATCAGC CAGCACCAAT      2517

TCCGGAAAAT TCAGAAATGG ATCAGGCTAA GGAAAAGGCT AAGATTGCTG TATCGAAGTA      2577

TATGAGTAAG GTTTTAGATG GAGTTCATCA ACATCTGCAG                            2617
```

( 2 ) INFORMATION FOR SEQ ID NO:2:

( i ) SEQUENCE CHARACTERISTICS:
        ( A ) LENGTH: 396 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Phe Lys Ser Asn Tyr Glu Arg Lys Met Arg Tyr Ser Ile Arg Lys
 1               5                  10                  15

Phe Ser Val Gly Val Ala Ser Val Ala Val Ala Ser Leu Phe Met Gly
                20                  25                  30

Ser Val Ala His Ala Ser Glu Leu Val Lys Asp Asp Ser Val Lys Thr
            35                  40                  45

Thr Glu Val Ala Ala Lys Pro Tyr Pro Ser Met Ala Gln Thr Asp Gln
50                  55                  60
```

```
Gly Asn Asn Ser Ser Ser Ser Glu Leu Glu Thr Thr Lys Met Glu Ile
 65              70              75                   80

Pro Thr Thr Asp Ile Lys Lys Ala Val Glu Pro Val Glu Lys Thr Ala
             85                   90                   95

Gly Glu Thr Ser Ala Thr Asp Thr Gly Lys Arg Glu Lys Gln Leu Gln
            100              105              110

Gln Trp Lys Asn Asn Leu Lys Asn Asp Val Asp Asn Thr Ile Leu Ser
         115              120              125

His Glu Gln Lys Asn Glu Phe Lys Thr Lys Ile Asp Glu Thr Asn Asp
        130              135              140

Ser Asp Ala Leu Leu Glu Leu Glu Asn Gln Phe Asn Glu Thr Asn Arg
145              150              155              160

Leu Leu His Ile Lys Gln His Glu Glu Val Glu Lys Asp Lys Lys Ala
             165              170              175

Lys Gln Gln Lys Thr Leu Lys Gln Ser Asp Thr Lys Val Asp Leu Ser
            180              185              190

Asn Ile Asp Lys Glu Leu Asn His Gln Lys Ser Gln Val Glu Lys Met
        195              200              205

Ala Glu Gln Lys Gly Ile Thr Asn Glu Asp Lys Asp Ser Met Leu Lys
        210              215              220

Lys Ile Glu Asp Ile Arg Lys Gln Ala Gln Gln Ala Asp Lys Lys Glu
225              230              235              240

Asp Ala Glu Val Lys Val Arg Glu Glu Leu Gly Lys Leu Phe Ser Ser
            245              250              255

Thr Lys Ala Gly Leu Asp Gln Glu Ile Gln Glu His Val Lys Lys Glu
            260              265              270

Thr Ser Ser Glu Glu Asn Thr Gln Lys Val Asp Glu His Tyr Ala Asn
        275              280              285

Ser Leu Gln Asn Leu Ala Gln Lys Ser Leu Glu Glu Leu Asp Lys Ala
    290              295              300

Thr Thr Asn Glu Gln Ala Thr Gln Val Lys Asn Gln Phe Leu Glu Asn
305              310              315              320

Ala Gln Lys Leu Lys Glu Ile Gln Pro Leu Ile Lys Glu Thr Asn Val
            325              330              335

Lys Leu Tyr Lys Ala Met Ser Glu Ser Leu Glu Gln Val Glu Lys Glu
            340              345              350

Leu Lys His Asn Ser Glu Ala Asn Leu Glu Asp Leu Val Ala Lys Ser
        355              360              365

Lys Glu Ile Val Arg Glu Tyr Glu Gly Lys Leu Asn Gln Ser Lys Asn
    370              375              380

Leu Pro Glu Leu Lys Gln Leu Glu Glu Glu Ala His
385              390              395
```